(12) United States Patent
Barth

(10) Patent No.: US 7,075,161 B2  
(45) Date of Patent: Jul. 11, 2006

(54) APPARATUS AND METHOD FOR MAKING A LOW CAPACITANCE ARTIFICIAL NANOPORE

(75) Inventor: Phillip W. Barth, Portola Valley, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/693,064

(22) Filed: Oct. 23, 2003

(65) Prior Publication Data

US 2005/0102721 A1 May 12, 2005

(51) Int. Cl.
  *H01L 27/14* (2006.01)
  *H01L 29/84* (2006.01)

(52) U.S. Cl. .............. 257/414; 257/419; 257/619; 438/53

(58) Field of Classification Search ........... 257/414, 257/419, 619; 438/53, 928, 977
See application file for complete search history.

(56) References Cited

U.S. PATENT DOCUMENTS

| 6,464,842 | B1* | 10/2002 | Golovchenko et al. 204/192.13 |
| 6,627,067 | B1* | 9/2003 | Branton et al. ............. 205/778 |
| 6,863,833 | B1* | 3/2005 | Bloom et al. .................. 216/2 |
| 2003/0032946 | A1* | 2/2003 | Fishman et al. ......... 604/890.1 |
| 2005/0009171 | A1* | 1/2005 | Fertig et al. ............. 435/287.2 |

OTHER PUBLICATIONS

Li et al., "Ion-Beam Sculpting At Nanometre Scales", Nature, vol. 412, Jul. 12, 2001, pp. 166-169.
Matzke et al., Title: "Integratible Process For Fabrication Of Fluidic Microduct Networks On A Single Wafer", Proceedings Of The SPIE-The International Society For Optical Engineering SPIE-Int. Soc. Opt. Eng USA, vol. 3877, 1999, pp. 110-118.
Copy of European Search Report Dated: Aug. 15, 2005.

* cited by examiner

*Primary Examiner*—Trung Dang

(57) ABSTRACT

An apparatus and method for making a nanopore chip exhibiting low capacitance. The apparatus provides a thin diaphragm on a rigid semiconductor frame suitable for nanopore fabrication, the diaphragm having associated thicker insulator regions to reduce capacitance. Also disclosed is a method of making the apparatus.

34 Claims, 11 Drawing Sheets

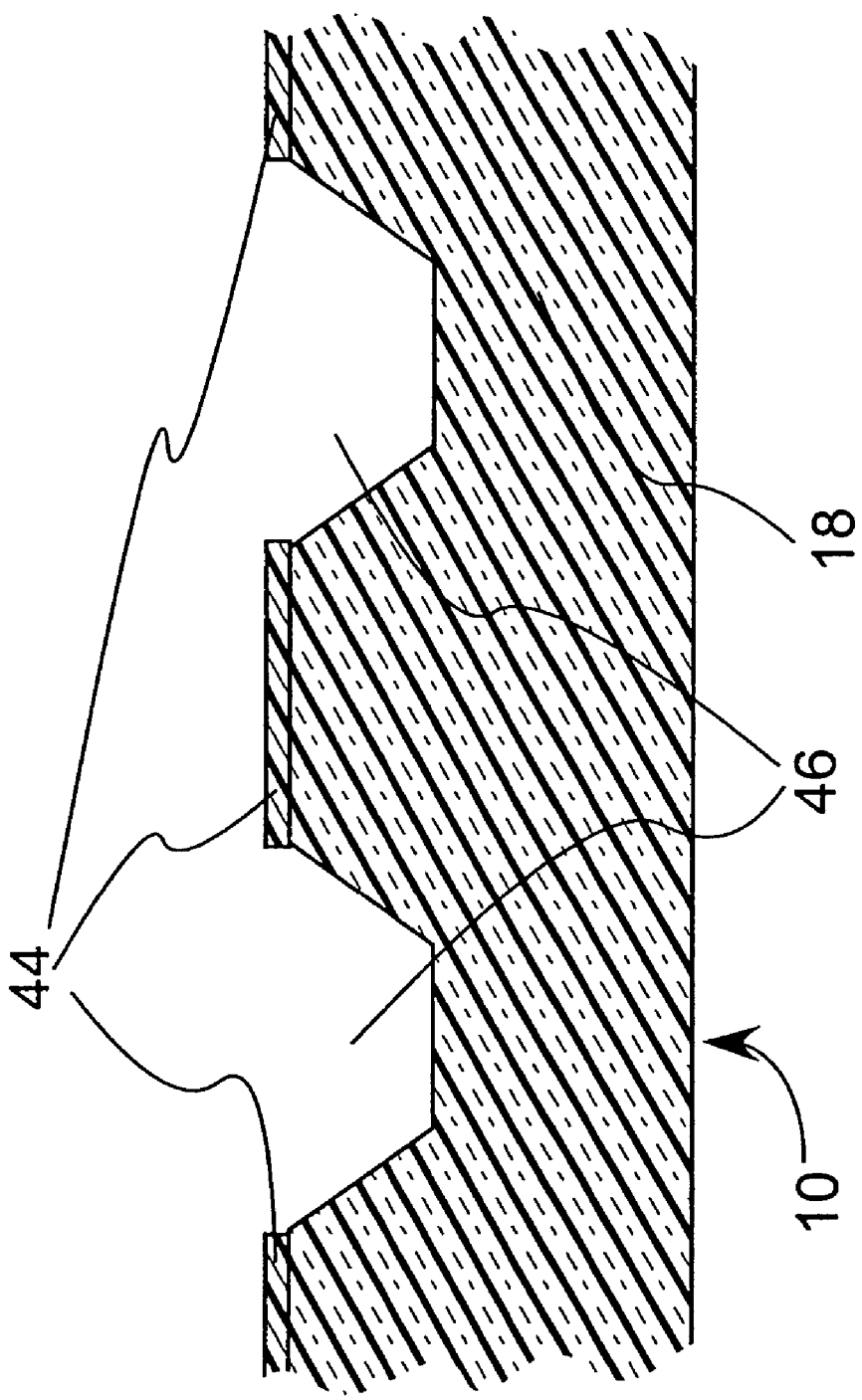

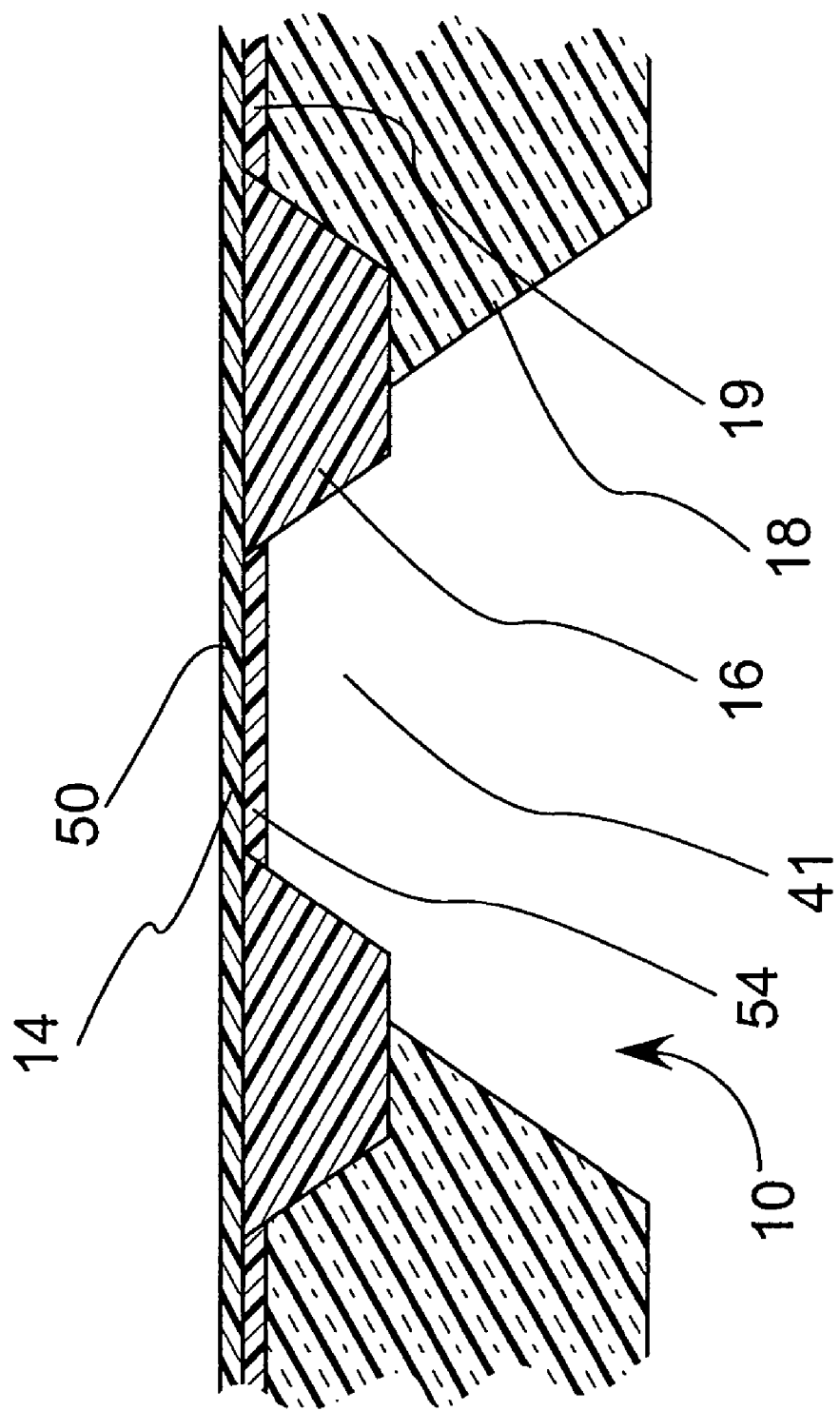

APPARATUS AND METHOD FOR MAKING A LOW CAPACITANCE ARTIFICIAL NANOPORE

TECHNICAL FIELD

The invention relates generally to the field of nanopores and more particularly to an apparatus and method for making a low capacitance artificial nanopore.

BACKGROUND

Manipulating matter at the nanometer scale is important for many electronic, chemical and biological advances (See Li et al., "Ion beam sculpting at nanometer length scales", *Nature*, 412: 166–169, 2001). Such techniques as "ion beam sculpting have shown promise in fabricating molecule scale holes and nanopores in thin insulating membranes. These pores have also been effective in localizing molecular-scale electrical junctions and switches (See Li et al., "Ion beam sculpting at nanometer length scales", *Nature*, 412: 166–169, 2001).

Artificial nanopores have been fabricated by a variety of research groups with a number of materials. Generally, the approach is to fabricate these nanopores in a solid-state material or a thin freestanding diaphragm of material supported on a frame of thick silicon to form a nanopore chip. Some materials that have been used to date for the diaphragm material include silicon nitride and silicon dioxide.

A problem with artificial nanopores fabricated on a silicon frame is that silicon is a semiconductor and has low resistivity, typically in the range of 1–50 Ohm-cm, which is much lower than the resistivity of a true insulator such as silicon nitride or silicon dioxide. For example, silicon nitride typically has a resistance greater than $10^{10}$ Ohm-cm while even high-resistivity silicon has a resistivity on the order of only $10^4$ Ohm-cm. Thus the silicon substrate can be considered to be a near short circuit for the purposes of capacitance calculation, and the resulting artificial nanopore on a silicon substrate, and any electrical leads associated with the nanopore, have undesirably high capacitance values. For example, if the silicon nitride layer is 200 nm thick and the contact area between the nanopore chip and a conductive liquid is a circle 1 mm in diameter, the capacitance across the insulator can approach 260 picoFarads (260 pF), which severely limits the frequency bandwidth for which electrical current through the nanopore can be measured.

This problem of high capacitance may be reduced, for a simple nanopore structure, by building an associated external package which limits the contact area between a conductive liquid and the nanopore substrate, so that total capacitance across the insulator is reduced to a value on the order of 1 picoFarad (1 pF). But using external packaging alone to produce a small liquid contact area is often difficult and problematic, and that approach ignores the need to place low-capacitance electrical leads on the surface of the insulator layer over the silicon frame. Therefore, an approach is needed which provides low capacitance for a relatively large liquid contact area to the insulator, and at the same time provides low capacitance for electrical leads running along the surface of the insulator.

These and other problems with the prior art processes and designs are obviated by the present invention. The references cited in this application infra and supra, are hereby incorporated in this application by reference. However, cited references or art are not admitted to be prior art to this application.

SUMMARY OF THE INVENTION

The invention provides an apparatus and method for nanopore construction.

It is to be understood that the terms used in the descriptive language below are described using the adjectives "first," "second," "third," "fourth," "fifth," "sixth," and the like, in order to describe the apparatus and method of the present invention in a manner consistent with a clear description of the apparatus, but not necessarily in an order related to the sequence of steps in the method of fabricating the apparatus. In particular, the use of these adjectives herein does not imply a numerical ordering herein, but is merely used as a verbal method of grouping; for example, the use of the word "third" to describe a particular feature does not necessarily imply the existence of a corresponding "second" feature.

The apparatus comprises a first region having the form of a diaphragm and comprising a first insulator material supported by a rigid frame, the rigid frame also supporting a second region comprising a second insulator much thicker than the diaphragm and lying beneath the plane of the diaphragm in order to provide low capacitance in the space beneath the plane of the diaphragm. The apparatus also comprises a third region comprising third insulator which is thicker than the diaphragm thickness, the third region lying atop the diaphragm and having a hole therethrough to expose the top entrance of a nanopore situated in the diaphragm. The third region also lies atop electrical leads and microfluidic leads disposed on the top surface of the diaphragm. The apparatus also comprises a fourth region comprising a fourth insulator disposed atop the third region, the fourth region being thicker than the third region and having a hole therethrough to expose a portion of the top surface of the third region. A fifth region comprising additional diaphragm material may be present in some embodiments. Sixth regions comprising insulator materials may be present in some embodiments of the invention to provide low capacitance beneath electrical leads or microfluidic leads in regions far from the diaphragm or far from the liquid contact area. In some embodiments one or more of the second, third, and fourth regions may be minimal or absent. In some embodiments one or more of electrical leads and microfluidic leads may be absent.

The invention also provides a method of making the apparatus. The method of making the apparatus comprises fabricating a nanopore chip by providing a semiconductor substrate, forming a second region comprising a second insulator material in a defined annular space beneath a substrate upper surface comprising an upper major surface of the substrate, the second region having an second region upper surface flush with the substrate upper surface, forming a fifth region which will sit beneath a diaphragm, forming sixth insulator regions which will sit beneath one of electrical leads and microfluidic leads, forming a layer comprising a first material atop the substrate upper surface and atop the second region upper surface, removing stock from the substrate beneath the annular space to expose a lower surface of the first material, thus forming a diaphragm, forming a nanopore in the diaphragm forming electrodes and electrode insulator regions associated with the nanopore, forming electrical leads associated with the nanopore, forming microfluidic leads associated with the nanopore, forming a layer of a third material atop the upper surface of the diaphragm and atop the electrical leads and microfluidic leads, forming a hole through the third material to expose an upper entrance of the nanopore, thereby establishing the shape of the third region forming a layer of a fourth material atop the third region, forming a hole through the fourth material to expose a portion of the upper surface of the third region, the hole through the fourth material having a larger diameter than the hole through the third material, thereby establishing the shape of the fourth region.

Subsequent to the steps of the above method, further fabrication and packaging of the device may occur, including but not limited to singulation of the multiple nanopore chips from the substrate into individual chip form, attachment of electrical wires, attachment of external fluidic channels to microfluidic channels, attachment of face-seal fluidic channels to top and bottom surfaces of the chip, introduction of electrical signals, introduction of chemical species, and recording of data by one or more of electrical, electronic, optical, chemical, and electrochemical means.

The steps of the above method may be varied in any logically consistent fashion. For example, the nanopore may be formed after the hole through the fourth material is formed. The hole through the third material may be formed after the hole through the fourth material is formed. One or both of the steps of forming electrical leads and microfluidic leads may be absent. The steps of forming electrodes and insulators associated with the electrodes may be varied or absent.

BRIEF DESCRIPTION OF THE FIGURES

The invention is described in detail below with reference to the following figures.

DETAILED DESCRIPTION OF THE INVENTION

Figure 1:
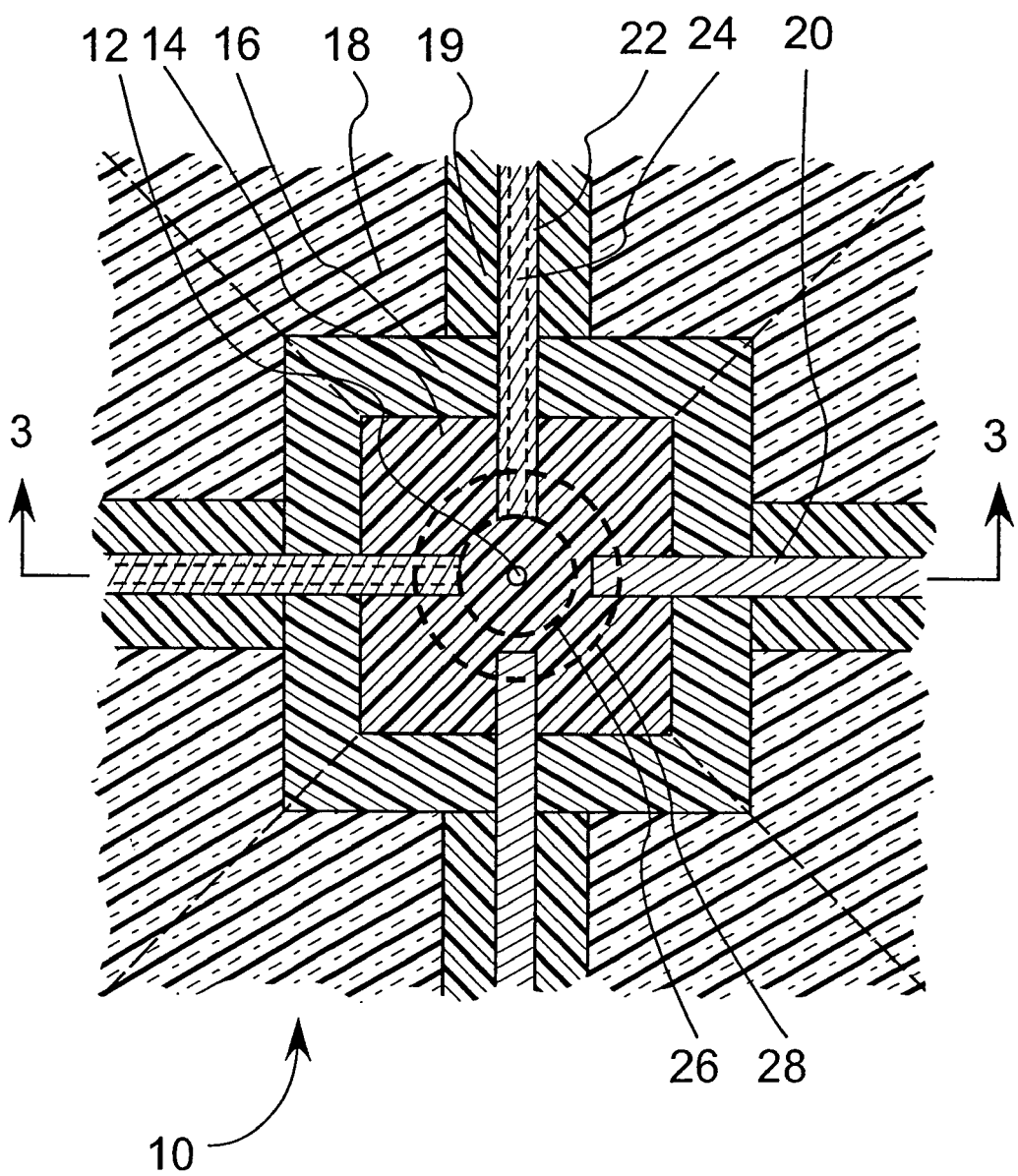
FIG. 1 shows a plan view of the apparatus 10 of the present invention, the viewpoint being at surface 1—1 shown in FIG. 3.

Before describing the present invention in detail, it is to be understood that this invention is not limited to specific compositions, method steps, or equipment, as such may vary. It is also to be understood that the terminology used herein is for the purpose of describing particular embodiments only, and is not intended to be limiting. Methods recited herein may be carried out in any order of the recited events that is logically possible, as well as the recited order of events.

Unless defined otherwise below, all technical and scientific terms used herein have the same meaning as commonly understood by one of ordinary skill in the art to which this invention belongs. Still, certain elements are defined herein for the sake of clarity. In the event that terms in this application are in conflict with the usage of ordinary skill in the art, the usage herein shall be controlling.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits; ranges excluding either or both of those included limits are also included in the invention.

Methods recited herein may be carried out in any order of the recited events that is logically possible, as well as the recited order of events.

It must be noted that, as used in this specification and the appended claims, the singular forms "a", "an," "the," and "one of" include plural referents unless the context clearly dictates otherwise.

The term "about" refers to being closely or approximate to, but not exactly. A small margin of error is present. This margin of error would not exceed plus or minus the same integer value. For instance, about 0.1 micrometers would mean no lower than 0 but no higher than 0.2.

The term "nanopore" refers to any pore or hole between at least a pair of electrodes or a hole in a solid substrate. Nanopores can range in size and can range from about 1 nm to about 300 nm. Most effective nanopores have been roughly around 2 nm.

The term "adjacent" refers to anything that is near, next to or adjoining. For instance, a tensile layer may be near a compressive layer, next to a compressive layer or adjoining a compressive layer.

The term "substantially flat" refers to a surface that is nearly flat or planar. In most cases, this term should be interpreted to be nearly or approximately uniformly flat. There are limited or no uneven surfaces.

The term "lateral extent" refers to a direction or directions lying substantially parallel to the substantially flat major surfaces of a component of a diaphragm, diaphragm component, or entire device. Thus, for example, a long thin finger of material meandering along a surface has a lateral extent that is small in relation to its overall length in a direction perpendicular to that length, and a lateral extent that is long in the direction of its length. Again, for example, an area of circular shape has a lateral extent that is uniform in all directions parallel to the major surface in which it lies.

It is to be understood that the terms used in the descriptive language below, and in the claims below, are described using the adjectives "first," "second," "third," "fourth," "fifth," "sixth," and the like, in order to describe the apparatus and method of the present invention in a manner consistent with a clear description of the apparatus, but not necessarily in an order related to the sequence of steps in the method of fabricating the apparatus. In particular, the use of these adjectives herein does not imply a numerical ordering herein, but is merely used as a verbal method of grouping; for example, the use of the word "third" to describe a particular feature does not necessarily imply the existence of a corresponding "second" feature. The use of such adjectives is consistent between the description of the apparatus, the description of the method, and the claims.

Figure 2:
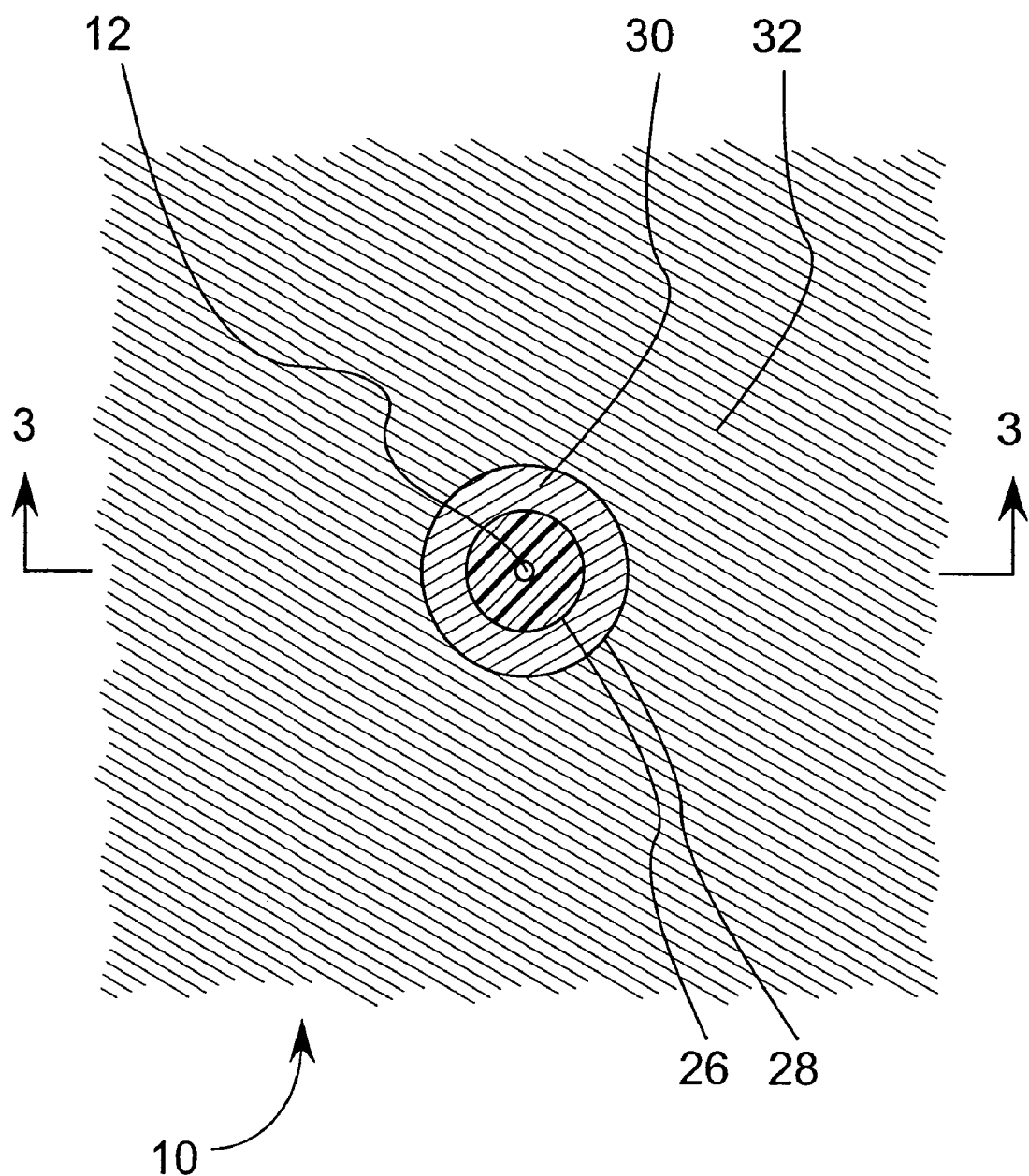
FIG. 2 shows a plan view of the apparatus 10 of the present invention, the viewpoint being at plane 2—2 shown in FIG. 3.
Figure 3:
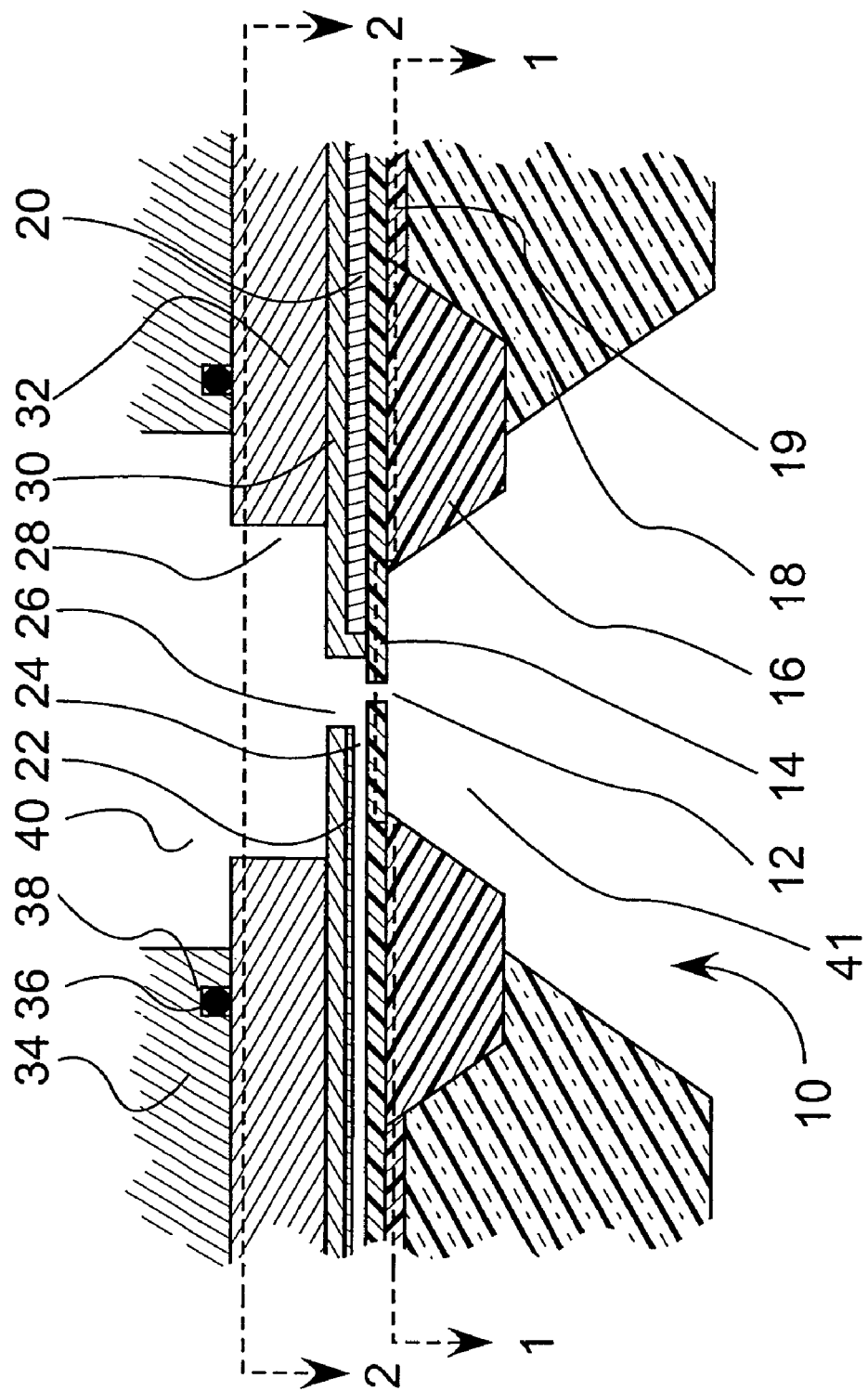
FIG. 3 shows a cross sectional view of the apparatus 10 of the present invention, the viewpoint being at plane 3—3 shown in FIG. 1

FIGS. 1–4 show the apparatus 10 of the present invention. FIG. 1 is a plan view of the apparatus 10 at surface 1—1 as shown in FIG. 3, and FIG. 2 is a plan view of the apparatus 10 at plane 2—2 as shown in FIG. 3. Surface 1—1 is not a plane but has an upward jog in the center of FIG. 3 in order to display features of the apparatus in a clear manner in FIG. 1. Surface 1—1 is rotationally symmetric about a vertical centerline, not shown, in FIG. 3. FIG. 3 is a cross section view at plane 3—3 shown in FIG. 1. FIGS. 4A–4H show steps in the method of fabricating the apparatus 10. The figures are not to scale, and some features are greatly exaggerated for purposes of description.

A nanopore 12 comprising a first hole extending through a diaphragm 14 is generally depicted in the figures, the diaphragm 14 being supported by a rigid frame comprising a semiconductor chip 18. The diaphragm 14 may range in lateral extent from 5 to at least 100 micrometers. The diaphragm 14 comprises a first insulator material, and typically comprises silicon nitride 200 nm thick. The diaphragm 14 may comprise an additional material or materials, not shown. The dimensions described here are for illustrative purposes only and should not be interpreted to limit the scope of invention.

A detailed description of the apparatus 10 of the invention is as follows, with reference to FIGS. 1–3. Nanopore 12 comprising a first hole is situated in diaphragm 14. Diaphragm 14 comprises a window comprising a first insulating material, and is supported within a collar comprising a second region 16 comprising a second insulating material. Second region 16 is supported in substrate 18 comprising a semiconductor, typically comprising silicon. A fifth insulator region, not shown in FIGS. 1–3 but shown in FIG. 4E as feature 54, may optionally comprise an additional part of the diaphragm. Sixth insulator regions 19 lie atop substrate 18 and beneath one of electrical leads 20 and microfluidic leads 22. Microfluidic channels 24 are situated within microfluidics leads 22. Third cavity 26, being typically 5 micrometers in diameter, and fourth cavity 28, being typically 60 micrometers in diameter, penetrate third region 30 and fourth region 32 respectively. Third region 30 comprises a third insulator material and is disposed atop features 14,16, 18,19,20, and 24. Fourth region 34 comprises a fourth insulator material and is disposed atop region 30. Feature 34 comprises an external package applied atop the apparatus 10. O-ring 36 sits in gland 38 and defines the area of contact of a liquid solution, not shown, disposed within package cavity 40 and making contact with regions 32, region 30, diaphragm 14, and nanopore 12. A liquid solution, not shown, also is disposed within substrate cavity 41 beneath diaphragm 14 and makes contact with diaphragm 14 and with nanopore 12. As shown, substrate cavity 41 extends entirely through substrate 18, but this is not a necessity of the invention. As shown, the lateral extent of the substrate cavity 41 near its top coincides with a portion of region 16, but this is not important and the lateral extent of the substrate cavity 41 near its top may instead or in addition coincide with a portion of diaphragm 14.

Electrical leads 20 closely approach nanopore 12 and can make contact, for example, to tunneling electrodes as described in detail in patent application Ser. No. 10/462,216, Filed on Jun. 12, 2003, NANOPORE WITH RESONANT TUNNELING ELECTRODES. That application describes both the structure and method of fabrication of resonant tunneling electrodes associated with a nanopores, and it will be appreciated, based on that description and on the description of apparatus 10 herein, that such resonant tunneling electrodes can be incorporated into apparatus 10.

Microfluidic channels 24 are disposed within microfluidic leads 22, and microfluidic channels 22 closely approach nanopore 12. Leads 22 and channels 24 can be fabricated by methods known to those skilled in microstructure fabrication. For example, leads 22 can comprise oxynitride deposited at a temperature of 90C atop preformed mandrel regions comprising positive photoresist, the mandrel regions later being removed by dissolution in acetone to form channels 24. The technique has been developed by Sandia researchers Carol Ashby and Carolyn Matzke and is detailed on the Web at http://www.sandia.gov/media/NewsRel/NR2000/canals.htm. Alternatively, leads 22 can comprise silicon dioxide deposited at a temperature of 250C atop preformed mandrel regions comprising polyimide, the polyimide later being removed by high-density oxygen plasma etching (see for example "Polyimide sacrificial layer and novel materials for post-processing surface micromachining," A Bagolini, et al., J. Micromech. Microeng. 12 (2002) 385–389) or by caustic etching (see, for example, http://www.dupont.com/ kapton/general/caustic-etching.pdf) to form channels 24. Parylene® may be used to form microfluidic leads 22 in a manner similar to that which has been reported in the literature, e.g. "Polymer-Based Electrospray Chips for Mass Spectrometry," Xuan-Qi Wang, et al., Proceedings, IEEE 12th International Micro Electro Mechanical Systems Conference (MEMS '99), Orlando, Fla., pp. 523–528, Jan. 17–21, 1999. Other variations on the materials and methods used to fabricate leads 22 and channels 24 will occur to those skilled in microstructure fabrication. Advantageously, leads 22 may comprise an insulating material, thus enabling a electric field to be established in a liquid solution filling channels 24. A combination of a hydraulic pressure drop along the length of channels 24 and an electric field along the length of channels 24 can advantageously quickly move molecules in solution within a liquid filling channels 24 to a position in close proximity to nanopore 12. The movement of such molecules can occur by a combination of pressure driven flow, electroosmotic flow, and electrophoretic flow, thus placing such molecules in close proximity to nanopore 12 much more quickly than could be achieved by diffusion of such molecules to the nanopore 12 from a more distant introduction point within either package cavity 40 or substrate cavity 41.

Region 30 comprises a third region comprising a third insulator material. Region 30 is depicted laying atop features 14,16,18,19,20, and 24. It should be appreciated that in some instances it may be desirable that the third insulator material comprise the walls of microfluidic leads 22, in which case the microfluidic leads 22 and the region 30 can comprise a unitary structure. Cavity 26 comprises a third cavity penetrating region 30 and providing an opening atop diaphragm 14 and atop nanopore 12.

Region 32 comprises a fourth region comprising a fourth insulator material. Cavity 28 comprises a fourth cavity penetrating region 32 and providing an opening atop region 30.

When the apparatus is in use, package cavity 40 and substrate cavity 41 are typically filled with a conductive ionic aqueous solution. It will be appreciated that capacitance across the diaphragm 14 between package cavity 40 and substrate cavity 41 is large if regions 16, 30, and 32 are absent. Such capacitance is smaller if region 30 is present, if region 30 is much thicker than diaphragm 14, and if cavity 26 has a small lateral extent. Such capacitance is also smaller if region 16 is present, if region 16 is much thicker than diaphragm 14, and if region 16 extends beyond the lateral extent of O-ring 36. Such capacitance is also smaller if region 32 is present, if region 32 is much thicker than diaphragm 14, and if cavity 28 has a small lateral extent.

Additionally, it will be appreciated that the capacitance between electrical leads 20 or microfluidic leads 22 and package cavity 40 is large if regions 30 and 32 are absent. Such capacitance is smaller if region 30 is present and thick, and such capacitance is smaller if region 32 is present and thick.

Likewise, it will be appreciated that the capacitance between electrical leads 20 or microfluidic leads 22 and substrate cavity 41 is large if regions 16 and 19 are absent. Such capacitance is smaller if region 16 is present and thick, and is smaller if regions 19 are present and thick.

The choice of materials for all regions of the apparatus depends on process compatibility considerations, electrical characteristics including permittivity and resistivity, and compatibility with use of the apparatus during measurement and cleaning. Diaphragm 14, typically comprising silicon nitride, may comprise one or more of one of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Region 16, typically comprising silicon dioxide, may comprise one or more of one of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Region 18, typically comprising silicon, comprises a semiconductor from a group including but not limited to silicon, germanium, and gallium arsenide. Electrical leads 20, typically comprising aluminum, comprise a conducting material which may comprise one of a metal, a silicide, an organic conductor and a superconductor, including but not limited to aluminum, gold, platinum, palladium, iridium, copper, chromium, and nickel. Microfluidic leads 22, typically comprising oxynitride, may comprise one or more of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Microfluidic channels 24 may be formed using mandrel materials comprising one or more of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Region 30, typically comprising polyimide, may comprise one or more of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Region 32, typically comprising polyimide, may comprise one or more of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Regions 19, typically comprising silicon dioxide, may comprise one or more of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal. Region 54 may comprise one or more of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, plasma nitride, an insulator, a semiconductor, and a metal.

Thus the apparatus of the invention can be optimized by choices of materials, region thicknesses, region lateral extents, and cavity lateral extents to provide desired minimal capacitances across the diaphragm 14 and from leads 20 and 22 to one or more of cavities 40 and 41.

It will be appreciated that, while electrical leads 20 and microfluidic leads 22 have been presented in FIGS. 1–3 and in the above description in positions immediately beneath the third region, this is not a necessity of the invention. Alternatively or in addition, leads 20 or 22 may be placed at locations including but not limited to atop the third region, atop the fourth region, in a recessed region of the substrate beneath the plane of the bottom surface of layer 50, and within the substrate cavity 41.

Having described the apparatus of the invention, a description of the method of fabrication of the invention is now in order. FIGS. 4A–4H show steps in the method of fabricating apparatus 10 of the invention.

Figure 4A:
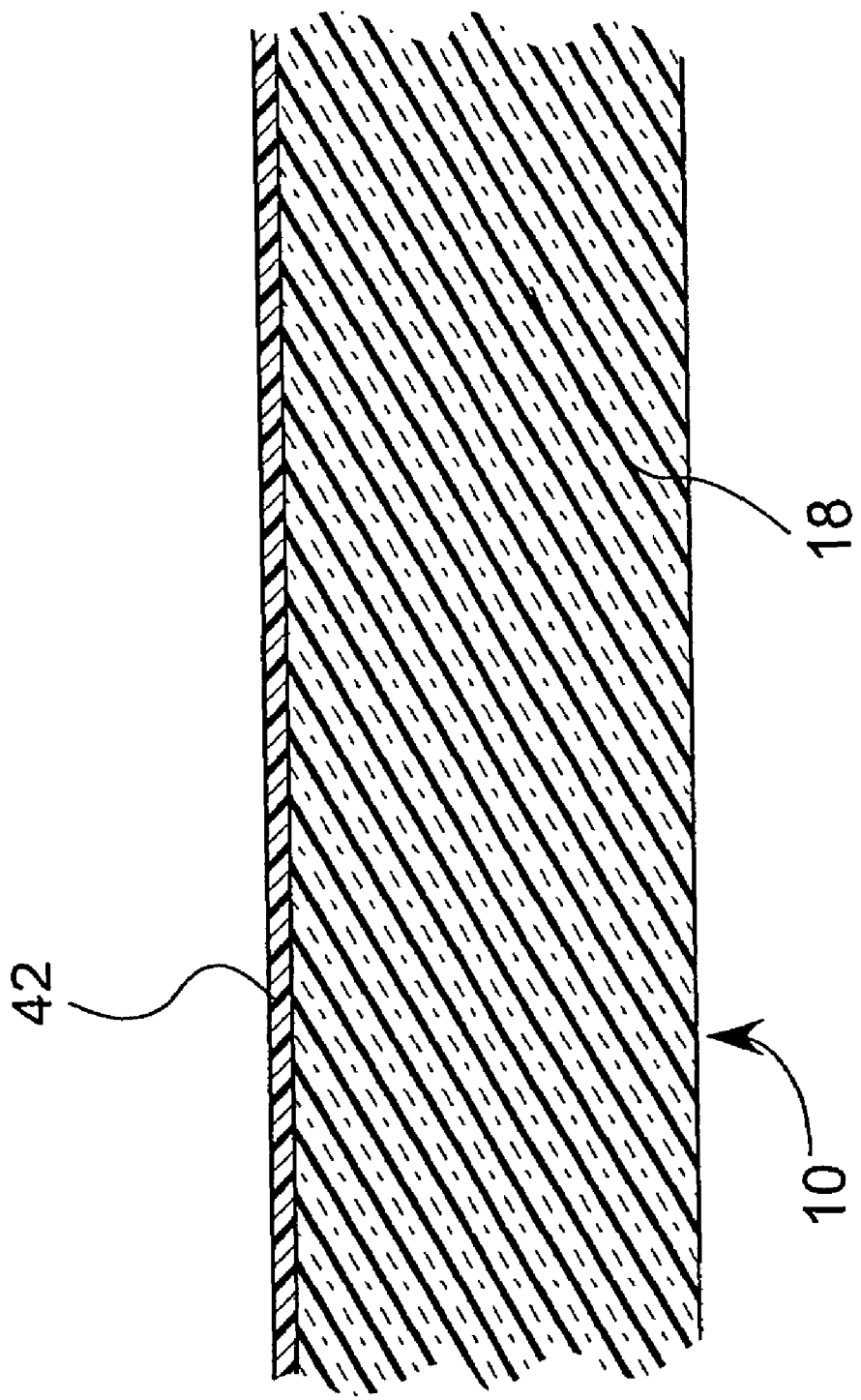
FIG. 4A shows a step of the method of the present invention.

The method begins as shown in FIG. 4A by providing a substrate 18 and forming a masking layer 42 comprising, for example, silicon dioxide, formed atop substrate 18.

The method continues as shown in FIG. 4B wherein layer 42 is defined, for example via lithography and etching, into masking regions 44. Cavity regions 46 are formed, for example by etching in a hot aqueous caustic solution of potassium hydroxide in water, and are etched to a depth of, for example, 10 micrometers.

Figure 4C:
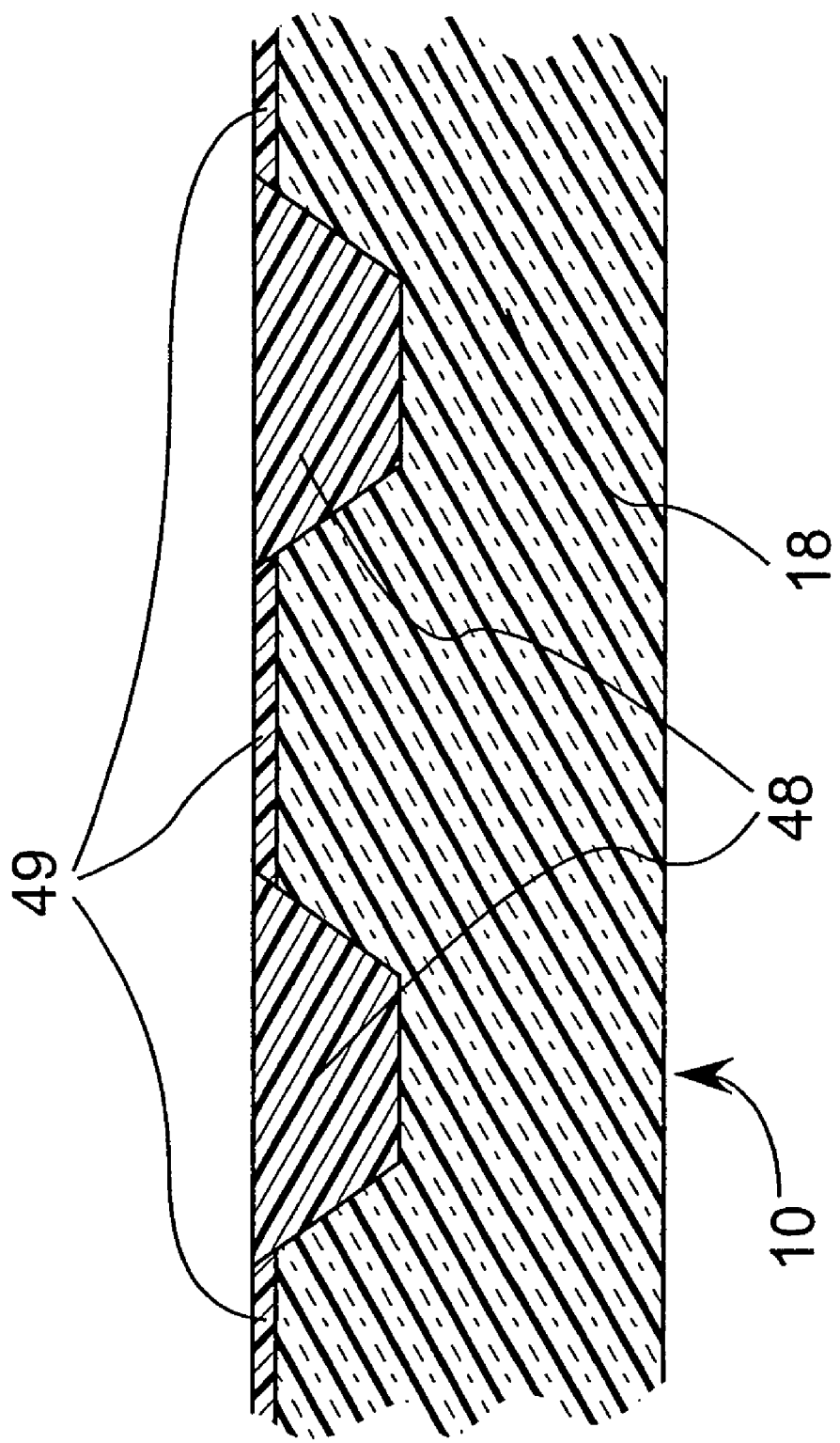
FIG. 4C shows a step of the method of the present invention.

The method continues as shown in FIG. 4C wherein cavity regions 46 are filled, typically by a deposition method such as TEOS oxide deposition, with the second insulator material forming insulator regions 48. It will be appreciated that between the structure shown in FIG. 4B and that shown in FIG. 4C, planarization of the upper surface of substrate 18 will typically occur via chemomechanical polishing (CMP). Regions 49 comprise fifth and sixth insulator materials, comprising for example thermally grown silicon dioxide, which is typically formed after CMP. It will be appreciated that the structure illustrated in FIG. 4C may be formed by use of the SUMMIT V fabrication process developed at Sandia Laboratories and commercialized by MEMX (see, for example, http://www.memx.com/technology.htm), or by other fabrication processes, and that at the same time one of active electrical circuitry and microstructures, not shown, may be fabricated one of in or on substrate 18 by use of the SUMMIT V process, or by other fabrication processes. At the same time regions 49 are formed, a layer of insulator, not shown, may be formed on the lower surface of substrate 18.

Figure 4D:
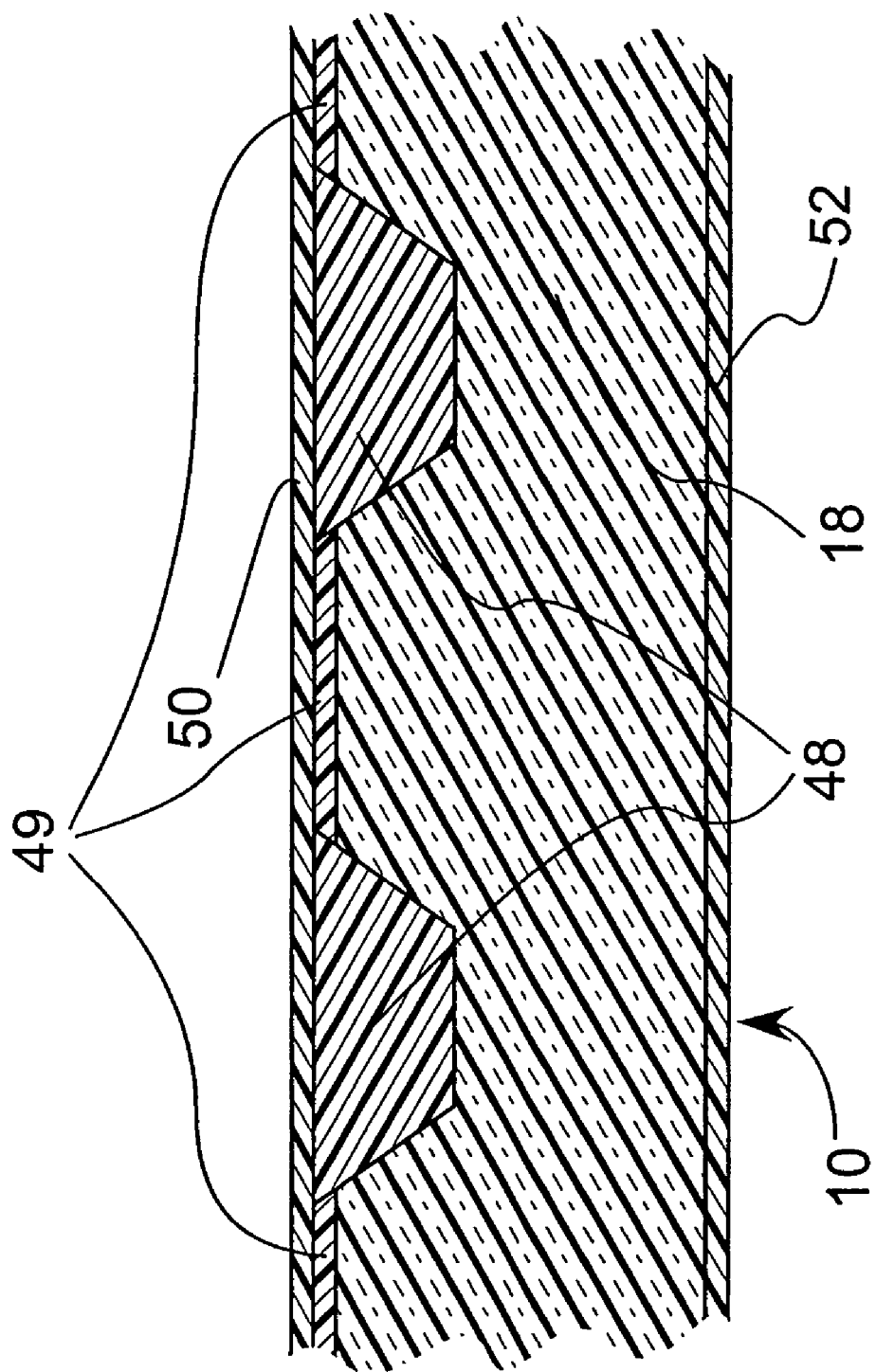
FIG. 4D shows a step of the method of the present invention.

The method continues as shown in FIG. 4D wherein layer 50, comprising the first insulating material, typically comprising silicon nitride, is formed atop regions 48 and 49, typically by means of low pressure chemical vapor deposition. Advantageously, at the same time as layer 50 is formed, a layer 52 is formed on the lower surface of substrate 18, or upon the exposed lower surface of any layers or structures which happen to be on the lower surface of substrate 18.

The method continues as shown in FIG. 4E wherein layer 52, no longer shown, has been formed, y by lithograph and plasma etching, into a masking region for the subsequent etching of substrate 18, typically in a hot aqueous caustic solution of potassium hydroxide, to form substrate cavity 41. Fifth region 54 comprises a fifth insulator material, comprising one or more of one of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, and plasma nitride. The lower surface of region 54, which was one of regions 49 in FIG. 4D, is exposed by the process of etching, while other parts of regions 49 now form regions 19 comprising sixth insulator regions as shown in FIGS. 1–3. The sixth insulator regions comprise one or more of one of a group including but not limited to a polymer, photoresist, SU8 photoresist, epoxy, polyimide, Parylene®, a silicone polymer, silicon dioxide, silicon nitride, silicon oxynitride, silicon-rich silicon nitride, TEOS oxide, and plasma nitride. Regions 48 now form region 16 as shown in FIGS. 1–3, and layer 50 has now been formed by the etching process into diaphragm 14 as shown in FIGS. 1–3.

Advantageously, region 54 may be left in place beneath diaphragm 14, region 54 and diaphragm 14 thereby forming a composite diaphragm, and such a composite diaphragm may be advantageously formed into a tensile diaphragm having a compressive region as described in patent application Ser. No. 10/670,554, Filed on Sep. 25, 2003— APPARATUS AND METHOD FOR MAKING A TENSILE DIAPHRAGM WITH A COMPRESSIVE REGION, the tensile diaphragm having a compressive region being used in subsequent steps of the present method in a manner not explicitly shown in the present application.

Alternatively and advantageously, region 54 may be left in place beneath diaphragm 14, region 54 and diaphragm 14 thereby forming a composite diaphragm, and such a composite diaphragm may be formed into a tensile diaphragm having an insert as detailed in patent application Ser. No. 10/670,551, Field on Sep. 25, 2003 APPARATUS AND METHOD FOR MAKING A TENSILE DIAPHRAGM WITH AN INSERT, the tensile diaphragm having an insert being used in subsequent steps of the present method in a manner not explicitly shown in the present application, and region 54 being removed at some later point in the fabrication process.

At the point in the fabrication process shown in FIG. 4E the nanopore 12 may be fabricated, then covered by later layers formed in the process and re-exposed near the end of the process. If electrodes associated with a nanopore are to be included in the apparatus of the invention as described in (Ser. No. 10/462,216, Filed on Jun. 12, 2003—Nanopore with resonant tunneling electrodes), then at this point in the method the nanopore may be fabricated and the electrodes and associated insulators may be fabricated. For simplicity of description, the fabrication of the nanopore, electrodes, and insulators are not described explicitly herein, but it will be appreciated that such fabrication can be performed in a manner described in (Ser. No. 10/426,216, Filed on Jun. 12, 2003—Nanopore with resonant tunneling electrodes). Alternatively, the fabrication of the nanopore, electrodes, and insulators can be begun at this point in the fabrication process and completed later in the fabrication process. Alternatively, and as illustrated in FIGS. 4F–4H, the fabrication of the nanopore can be delayed to later in the fabrication process.

Figure 4F:
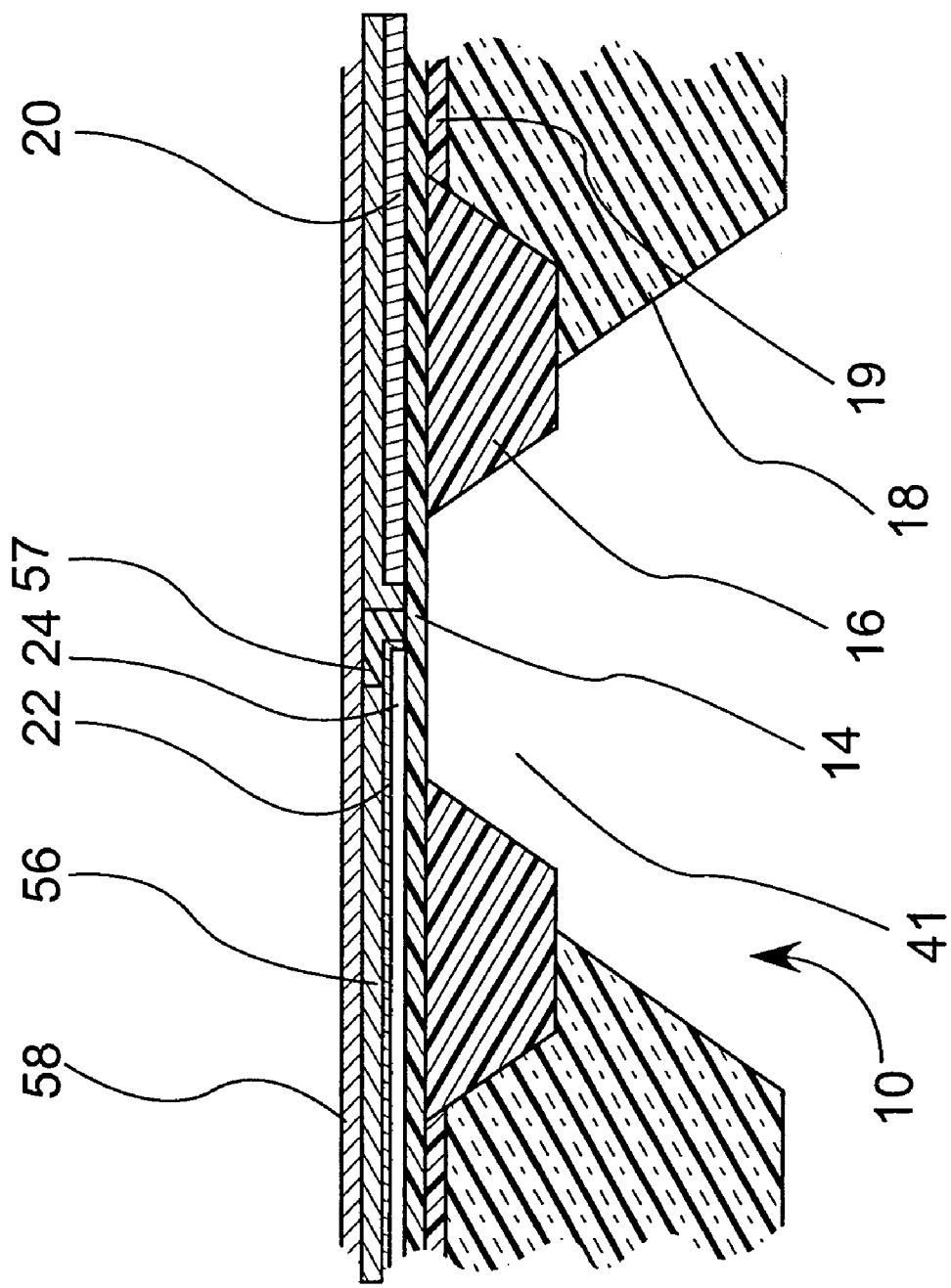
FIG. 4F shows a step of the method of the present invention.

The method continues as shown in FIG. 4F wherein region 54 is removed for purposes of simple description of the fabrication method. Electrical leads 20 and microfluidic leads 22 having microfluidic channels 24 are fabricated using techniques available to those skilled in the art. In particular, microfluidic channels 24 may be opened by use of a clearing technique as discussed above such as acetone dissolving, oxygen plasma etching, or caustic etching, before subsequent layers are deposited above microfluidic channels 22, but in the local area of channels 22 beneath region 57 there may advantageously be no openings into which fluid can intrude. This lack of opening in the area beneath region 57 can be achieved by having the horizontal one of channels 22 as shown in FIG. 1 connect with the vertical one of channels 22 as shown in FIG. 1 at the stage of the fabrication process shown in FIG. 4F. On the nanopore chip in regions far from the nanopore the unseen ends of microfluidic channels 24, to which external fluidic connections may later be made, can be occluded by one or more of various methods to prevent later deposited layers from intruding into them.

Layer 56, typically comprising polyimide, typically about 2 micrometers thick, comprises the third insulator material, and is later to be shaped to form region 30. Region 57 is a portion of layer 56 later to be removed to form cavity 26 shown in FIGS. 1–3. Layer 58, typically comprising aluminum, is a masking material which will later serve as an etch-stop layer during fabrication of cavity 28 shown in FIGS. 1–3. Layer 58 may comprise one of a group including but not limited to a metal, a polymer, photoresist, SU8 photoresist, epoxy, polyimide, Parylene®, a silicone polymer, silicon dioxide, silicon nitride, silicon oxynitride, silicon-rich silicon nitride, TEOS oxide, and plasma nitride. Advantageously, in some instances layer 56 may comprise a photosensitive material, so that region 57 may be defined by a photolithographic exposure, without at this time performing a developing step, leaving a region to be developed away later, before layer 58 is deposited. In such a case layer 58 can advantageously comprise an opaque material, for instance a metal such as aluminum. Alternatively, a hole, not shown, may be formed in layer 58 over region 57 to allow later etching of region 57.

Figure 4G:
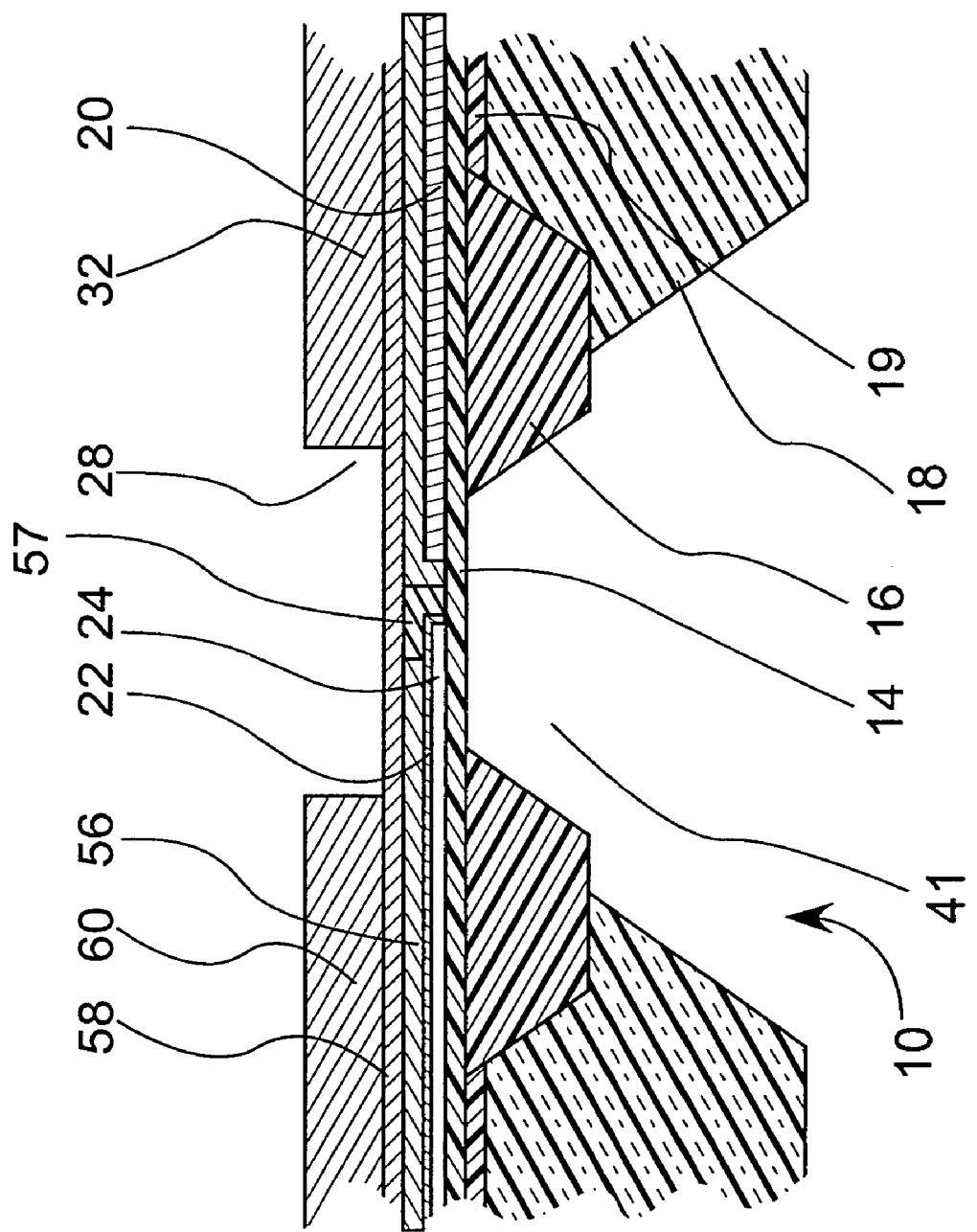
FIG. 4G shows a step of the method of the present invention.
Figure 4H:
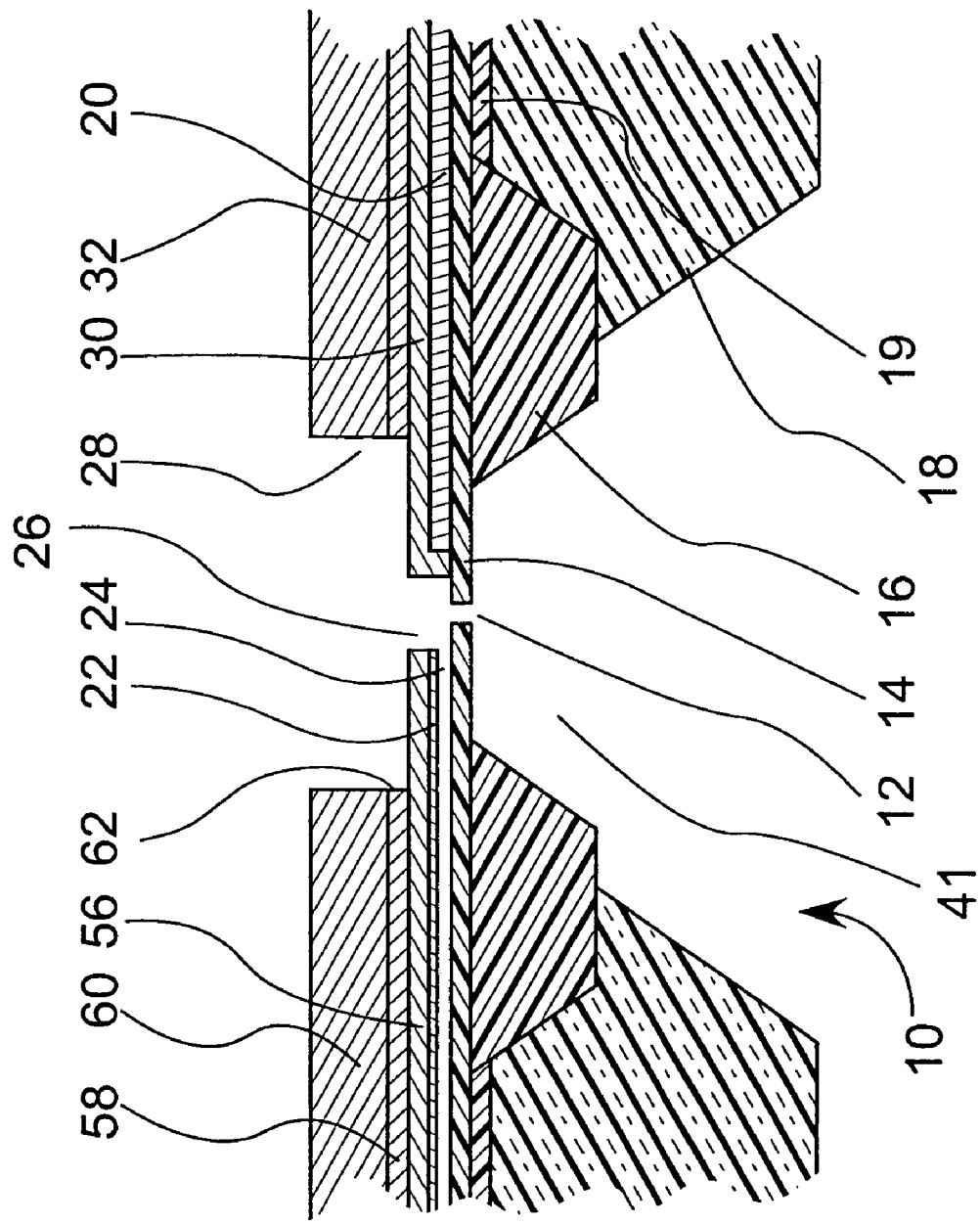
FIG. 4B shows a step of the method of the present invention.
FIG. 4E shows a step of the method of the present invention.

The method continues as shown in FIG. 4G. A layer 60, typically comprising polyimide, typically about 25 micrometers thick, comprising a fourth insulator material has been formed on top of layer 58, and fourth cavity 28 has been formed in layer 58 to define region 32. Layer 58 at the bottom of fourth cavity 28 serves as an etch stop layer.

The method continues to a final form of apparatus 10 as shown in FIG. 4H. If a hole, not shown, has been previously formed in region 58 over region 57 as discussed above, and if the third insulator material comprising layer 56 has similar etching characteristics to the material of layer 60, then etching can simply continue through the hole in layer 58 to remove region 57, forming cavity 26 comprising a third cavity. The portion of layer 58 at the bottom of cavity 28 is then etched away to edge 62. The microfluidic leads 22 in the region beneath cavity 26 are then etched, opening microfluidic channels 24 in the region beneath cavity 26 and leaving the opened local ends of channels 22 self aligned with the edges of cavity 26. Those portions of layer 58 not etched away remain in place, but are not explicitly shown in FIGS. 1–3. Nanopore 12 is then formed, for example by focused ion beam machining followed by argon ion beam sculpting, producing the final device structure as shown in FIG. 4H.

If no hole had been formed in layer 58 before etching of cavity 28, but a previous photolithographic exposure had been performed of region 57, then after cavity 28 is formed the portion of layer 58 at the bottom of cavity 28 is etched away. The photolithographically exposed region 57 is then developed away, and the microfluidic leads 22 in the region beneath cavity 26 are then etched, opening microfluidic channels 24 in the region beneath cavity 26 and leaving the opened local ends of channels 22 self aligned with the edges of cavity 26. Again, those portions of layer 58 not etched away remain in place, but are not explicitly shown in FIGS. 1–3. Nanopore 12 is then formed, for example by focused ion beam machining followed by argon ion beam sculpting, producing the final device structure as shown in FIG. 4H.

It will be appreciated that the fabrication sequence described above is by way of example only, and that there are others techniques well known to those skilled in the art which may be used to arrive at the same final structure. It will be appreciated also that the use of known adhesion promoter techniques between various layers will improve the yield of the fabrication process and the quality of the finished nanopore chip, and the use of such adhesion promoter techniques is assumed during the fabrication process even where not explicitly described.

It will be appreciated that the fabrication of a nanopore may be accomplished by means other than focused ion beam drilling and argon ion beam sculpting. For example, other known means of fabricating a nanopore include masking with a nanoparticle followed by layer evaporation around the masking nanoparticle, next followed by removal of the nanoparticle and etching within the hole that had been masked by the nanoparticle. Such techniques, both known and unknown may be used to fabricate nanopores within the compressive region 7 of the present invention.

It will be appreciated that, while the present invention is aimed toward utility in fabrication of nanopore structures, it may prove to have utility for fabrication of other devices both known and unknown. Such devices include devices with microscale and nanoscale dimensions. Microscale dimensions are defined to include dimensions from 100 nm to 1 mm, and nanoscale dimensions are defined to include dimension from 0.1 nm to 1 um.

I claim:

1. An apparatus for the construction of one of a microscale and nanoscale device, comprising:
   a first region comprising a diaphragm, the diaphragm comprising a first insulator material, the diaphragm having a top surface and a bottom surface,
   a second region comprising a second insulator material laterally surrounding the first region and having an upper surface substantially flush with the bottom surface of the first region,
   a substrate region comprising semiconductor material supporting the first region, the semiconductor material comprising a rigid frame laterally surrounding the diaphragm, wherein the second region is positioned between a portion of the bottom surface of the first region and a portion of an upper surface of the substrate region,
   a substrate cavity region beneath the diaphragm,
   a third region comprising a third insulator material, the third region being disposed atop the diaphragm, the third region being substantially thicker than the diaphragm and having a third cavity therethrough exposing a portion of the top surface of the diaphragm, the exposed portion of the top surface of the diaphragm being suitable for fabrication of one of a microscale and a nanoscale device.

2. A structure as recited in claim 1, wherein the one of a microscale and a nanoscale device comprises a first hole extending through the diaphragm.

3. A structure as recited in claim 1, wherein the one of a microscale and a nanoscale device comprises a nanopore.

4. A structure as recited in claim 1, wherein the second region is substantially thicker than the first region.

5. A structure as recited in claim 1, further comprising a fourth region comprising a fourth insulator material disposed atop the third region, the fourth region being substantially thicker than the first region and having a fourth cavity therethrough exposing a portion of the top surface of the third region surrounding the third cavity.

6. A structure as recited in claim 1, further comprising a fifth material, the fifth material comprising a bottom layer portion of the diaphragm.

7. A structure as recited in claim 1, further comprising a sixth region comprising a sixth insulator material disposed atop the substrate region.

8. A structure as recited in claim 1, wherein the first region comprises one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a polymer, a semiconductor, and a metal.

9. A structure as recited in claim 1, wherein the first region comprises silicon nitride.

10. A structure as recited in claim 1, wherein the third region comprises one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a semiconductor, and a metal.

11. A structure as recited in claim 6, wherein the fourth region comprises one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a semiconductor, and a metal.

12. A structure as recited in claim 5, wherein the fourth region comprises one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a semiconductor, and a metal.

13. A structure as recited in claim 1, wherein the diaphragm is from 50 nm to 500 nm in thickness.

14. A structure as recited in claim 1, wherein the diaphragm is about 200 nm thick.

15. A structure as recited in claim 1, wherein the third region is from 1 to 50 micrometers in thickness.

16. A structure as recited in claim 1, wherein the third region is about 2 micrometers thick.

17. A structure as recited in claim 4, wherein the second region is from 1 to 20 micrometers in thickness.

18. A structure as recited in claim 4, wherein the second region is from about 10 micrometers thick.

19. A structure as recited in claim 5, wherein the fourth region is from 1 to 50 micrometers in thickness 20. A structure as recited in claim 5, wherein the fourth region is about 25 micrometers thick.

21. A structure as recited in claim 1, wherein the semiconductor material comprises one of silicon, germanium, and gallium arsenide.

22. A structure as recited in claim 6 wherein the fifth material comprises one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a semiconductor, and a metal.

23. A structure as recited in claim 7 wherein the sixth material comprises one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a semiconductor, and a metal.

24. A structure as recited in claim 1, further comprising one of electrical leads and microfluidic leads, said lead being disposed at a location comprising one of beneath the third region, atop the third region, atop the fourth region, beneath the plane of the bottom surface of the diaphragm, and within the substrate cavity.

25. A structure as recited in claim 24, further comprising an electrical lead comprising one of a metal, a silicide, an organic conductor, a superconductor, aluminum, gold, platinum, palladium, iridium, copper, chromium, and nickel.

26. A structure as recited in claim 24, further comprising a microfluidic lead comprising one of a polymer, photoresist, SU8 photoresist, epoxy, polyimide, poly para-xylene, a silicone polymer, silicon dioxide, silicon nitride, silicon oxynitride, silicon-rich silicon nitride, TEOS oxide, plasma nitride, an insulator, a semiconductor, and a metal.

27. An apparatus for the construction of one of a microscale and nanoscale device, comprising:
  a first region comprising a diaphragm, the diaphragm comprising a first insulator material, the diaphragm having a top surface and a bottom surface,
  a second region comprising a second insulator material laterally surrounding the first region and having an upper surface substantially flush with the bottom surface of the first region,
  a substrate region comprising semiconductor material supporting the first region, the semiconductor material comprising a rigid frame laterally surrounding the diaphragm, wherein the second region is positioned between a portion of the bottom surface of the first region and a portion of an upper surface of the substrate region,
  a substrate cavity region beneath the diaphragm,
  a third region comprising a third insulator material, the third region being disposed atop the diaphragm, the third region being substantially thicker than the diaphragm and having a third cavity therethrough exposing a portion of the top surface of the diaphragm, the exposed portion of the top surface of the diaphragm being suitable for fabrication of one of a microscale and a nanoscale device,
  wherein the third insulator material provides for low-capacitance across the top surface of the diaphragm.

28. A structure as recited in claim 27, wherein the one of a microscale and a nanoscale device comprises a nanopore.

29. A structure as recited in claim 27, further comprising a fourth region comprising a fourth insulator material disposed atop the third region, the fourth region being substantially thicker than the first region and having a fourth cavity therethrough exposing a portion of the top surface of the third region surrounding the third cavity.

30. A structure as recited in claim 27, further comprising a fifth material, the fifth material comprising a bottom layer portion of the diaphragm.

31. A structure as recited in claim 27, further comprising a sixth region comprising a sixth insulator material disposed atop the substrate region.

32. An apparatus for the construction of one of a microscale and nanoscale device, comprising:
  a first region comprising a diaphragm, the diaphragm comprising a first insulator material, the diaphragm having a top surface and a bottom surface,
  a second region comprising a second insulator material laterally surrounding the first region and having an upper surface substantially flush with the bottom surface of the first region,
  a substrate region comprising semiconductor material supporting the first region, the semiconductor material comprising a rigid frame laterally surrounding the diaphragm, wherein the second region is positioned between a portion of the bottom surface of the first region and a portion of an upper surface of the substrate region,
  a substrate cavity region beneath the diaphragm,
  a third region comprising a third insulator material, the third region being disposed atop the diaphragm, the third region being substantially thicker than the diaphragm and having a third cavity therethrough exposing a portion of the top surface of the diaphragm, the exposed portion of the top surface of the diaphragm being suitable for fabrication of one of a microscale and a nanoscale device, and
  a microfluidic lead, said lead being disposed at a location comprising one of beneath the third region, and atop the third region.

33. An apparatus for the construction of one of a microscale and nanoscale device, comprising:
  a first region comprising a diaphragm, the diaphragm comprising a first insulator material, the diaphragm having a top surface and a bottom surface,
  a second region comprising a second insulator material laterally surrounding the first region and having an upper surface substantially flush with the bottom surface of the first region,
  a substrate region comprising semiconductor material supporting the first region, the semiconductor material comprising a rigid frame laterally surrounding the diaphragm, wherein the second region is positioned between a portion of the bottom surface of the first region and a portion of an upper surface of the substrate region,
  a substrate cavity region beneath the diaphragm,
  a third region comprising a third insulator material, the third region being disposed atop the diaphragm, the third region being substantially thicker than the diaphragm and having a third cavity therethrough exposing a portion of the top surface of the diaphragm, the exposed portion of the top surface of the diaphragm being suitable for fabrication of one of a microscale and a nanoscale device, and
  a fifth material, the fifth material comprising a bottom layer portion of the diaphragm.

34. An apparatus for the construction of one of a microscale and nanoscale device, comprising:
  a first region comprising a diaphragm, the diaphragm comprising a first insulator material, the diaphragm having a top surface and a bottom surface, a second region comprising a second insulator material laterally surrounding the first region and having an upper surface substantially flush with the bottom surface of the first region, a substrate region comprising semiconductor material supporting the first region, the semiconductor material comprising a rigid frame laterally surrounding the diaphragm, wherein the second region is positioned between a portion of the bottom surface of the first region and a portion of an upper surface of the substrate region, a substrate cavity region beneath the diaphragm, a third region comprising a third insulator material, the third region being disposed atop the diaphragm, the third region being substantially thicker than the diaphragm and having a third cavity therethrough exposing a portion of the top surface of the diaphragm, the exposed portion of the top surface of the diaphragm being suitable for fabrication of one of a microscale and a nanoscale device, and a sixth region comprising a sixth insulator material disposed atop the substrate region.

* * * * *